United States Patent [19]

Larsen et al.

[11] Patent Number: 5,793,827
[45] Date of Patent: Aug. 11, 1998

[54] MATERIAL SURVEILLANCE SPECIMEN HOLDER FOR CORE SHROUD OF BOILING WATER REACTOR

[75] Inventors: Karl Bomann Larsen; Charles Arthur Dalke, both of San Jose, Calif.

[73] Assignee: General Electric Company, San Jose, Calif.

[21] Appl. No.: 532,183

[22] Filed: Sep. 22, 1995

[51] Int. Cl.$^6$ .................. G21C 9/00; G21C 17/00; G01N 17/00
[52] U.S. Cl. ................ 376/255; 376/202; 376/245; 376/341; 73/86
[58] Field of Search ................ 376/153–155, 376/202, 245, 254, 255, 341; 220/23.2, 23.4, 23.8; 73/86, 760, 866.5

[56] References Cited

U.S. PATENT DOCUMENTS

| | | |
|---|---|---|
| 4,195,868 | 4/1980 | Kalen et al. ............ 376/202 X |
| 4,195,869 | 4/1980 | Klahn et al. ............ 376/202 X |
| 4,196,047 | 4/1980 | Mitchem et al. ........ 376/202 X |
| 4,945,758 | 8/1990 | Carpenter ............... 73/86 |
| 5,349,874 | 9/1994 | Schapira et al. ........ 73/86 X |

*Primary Examiner*—Charles T. Jordan
*Assistant Examiner*—Matthew J. Lattig
*Attorney, Agent, or Firm*—James E. McGinness; Dennis M. Flaherty

[57] ABSTRACT

A device for carrying out a surveillance program to monitor the environmental effect of radiation and high-temperature oxygenated water on the shroud material in an operating reactor. The device is a holder containing shroud material specimens and encapsulated neutron flux monitors. The holder is installed on the shroud wall and left in place for a predetermined period of reactor operation time for the purpose of monitoring the neutron fluence effect on the shroud material specimens housed in the holder. The specimen holder is later removed from the reactor. The specimens are removed from the holder and examined in a laboratory to determine any changes in material properties. The specimen holder comprises a bolt-like device having a hollow head and a threaded shaft. The hollow head provides space for material specimens and neutron flux monitors. The specimen holder is attached to the shroud wall by screwing the threaded shaft into a threaded hole in shroud wall.

10 Claims, 3 Drawing Sheets

MATERIAL SURVEILLANCE SPECIMEN HOLDER FOR CORE SHROUD OF BOILING WATER REACTOR

FIELD OF THE INVENTION

This invention is directed to devices that measure and monitor stress corrosion cracking of structural components within aggressive service environments, such as light water nuclear reactors. In particular, the invention relates to devices which measure the susceptibility to irradiation-assisted stress corrosion cracking of the core shroud of a boiling water reactor.

BACKGROUND OF THE INVENTION

When some structural materials are exposed to nuclear reactor service environments under steady or cyclic stress, irradiation-assisted stress corrosion cracking (IASCC) can occur. It is desirable to monitor and assess the extent of damage to structural components due to IASCC, for example, in a boiling water reactor (BWR) which has been operating for a number of years, to help predict its lifetime.

One type of a boiling water reactor is shown in FIG. 1. Feedwater is admitted into a reactor pressure vessel (RPV) 10 via a feedwater inlet 12 and a feedwater sparger 14, which is a ring-shaped pipe having suitable apertures for circumferentially distributing the feedwater inside the RPV. The feedwater from sparger 14 flows downwardly through the downcomer annulus 16, which is an annular region between RPV 10 and core shroud 18.

Core shroud 18 is a stainless steel cylinder surrounding the nuclear fuel core 20. Core 20 is made up of a plurality of fuel bundle assemblies 22 (only two 2×2 arrays of which are shown in FIG. 1). Each array of fuel bundle assemblies is supported at the top by a top guide 19 and at the bottom by a core plate 21.

The water flows through downcomer annulus 16 to the core lower plenum 24. The water subsequently enters the fuel assemblies 22, wherein a boiling boundary layer is established. A mixture of water and steam enters core upper plenum 26 under shroud head 28. Vertical standpipes 30 atop shroud head 28 are in fluid communication with core upper plenum 26. The steam-water mixture flows through standpipes 30 and enters steam separators 32. The separated liquid water then mixes with feedwater in the mixing plenum 40, which mixture then returns to the core via the downcomer annulus. The steam passes through steam dryers 34 and enters steam dome 36. The steam is conducted from the RPV via steam outlet 38.

The BWR also includes a coolant recirculation system which provides the forced convection flow through the core necessary to attain the required power density. A portion of the water is sucked from the lower end of the downcomer annulus 16 via recirculation water outlet 42 and forced by a centrifugal recirculation pump (not shown) into jet pump assemblies 44 (only one of which is shown) via recirculation water inlets 46. The BWR has two recirculation pumps, each of which provides the driving flow for a plurality of jet pump assemblies. The jet pump assemblies are circumferentially distributed around the core shroud 18.

The core shroud 18 (see FIG. 2) comprises a shroud flange 18a for supporting the shroud head 28; a circular cylindrical upper shroud wall 18b having a top end welded to shroud flange 18a; an annular top guide support ring 18c welded to the bottom end of upper shroud wall 18b; a circular cylindrical middle shroud wall comprising three sections 18d,

2

18e and 18f welded in series, with a top end of section 18d being welded to top guide support ring 18c; and an annular core plate support 18g welded to the bottom end of middle shroud wall section 18f and to the top end of a lower shroud wall 18h. Typically, the shroud sections are made of Type 304 or 316 stainless steel. The entire shroud is supported by a core support ring 50, which is welded to the bottom of lower shroud wall 18h, and by annular shroud support plate 52, which is welded at its inner diameter to core support ring 50 and at its outer diameter to RPV 10. The support support plate 52 is supported by shroud support legs 48 that are welded to the core support ring 50 and the RPV 10.

The various weldments of the shroud and the heat affected zones of those weldments are susceptible to IASCC. Stress corrosion cracking in the heat affected zone of any shroud girth seam welds diminishes the structural integrity of shroud 18, which vertically and horizontally supports core top guide 19, core plate 21 and shroud head 28. In particular, a cracked shroud increases the risks posed by a loss-of-coolant accident (LOCA). During a LOCA, the loss of coolant from the reactor pressure vessel produces a loss of pressure above the shroud head 28 and an increase in pressure inside the shroud, i.e., underneath the shroud head. The result is an increased lifting force on the shroud head and on the upper portions of the shroud to which the shroud head is bolted. If the core shroud has fully cracked girth welds, the lifting forces produced during a LOCA could cause the shroud to separate along the areas of cracking, causing the nuclear fuel core 20 to lose its lateral support.

Irradiation-assisted stress corrosion cracking can progress to the stage where mechanical repair is required to allow a plant to return to power. Such repair takes several months to plan and implement, resulting in significant unplanned outage time. Because of the potential detrimental impact of shroud cracking on BWR operation, a need exists to monitor the environmental effect on core shroud material of radiation and high-temperature water with high oxygen content.

SUMMARY OF THE INVENTION

The present invention is a device for carrying out a surveillance program to monitor the environmental effect of radiation and high-temperature water with high oxygen content on the shroud material in an operating reactor. The device is a holder containing shroud material specimens and encapsulated neutron flux monitors. The holder is installed on the shroud wall and left in place for a predetermined period of reactor operation time for the purpose of monitoring the neutron fluence effect on the shroud material specimens housed in the holder. For example, the specimen holder can be threaded into a recess in the shroud wall.

After the surveillance period has terminated, the specimen holder can be removed from the reactor. Then the specimens are removed from the holder and examined in a laboratory to determine any changes in material properties.

In accordance with one preferred embodiment of the invention, the specimen holder is a leaktight container that protects the material specimens housed therein from the reactor coolant. The leaktight specimen holder comprises a bolt-like device having a hollow head and a threaded shaft. The hollow head provides space for material specimens and encapsulated neutron flux monitors. The specimen holder is attached to the shroud wall by screwing the threaded shaft into a threaded hole, which may be formed in the shroud wall using conventional techniques.

In accordance with another preferred embodiment of the invention, the specimen holder is an open container that exposes the material specimens housed therein to the reactor coolant. The open specimen holder comprises a bolt-like device having a hollow head and a threaded shaft—similar to the leaktight specimen holder. The open specimen holder differs from the leaktight specimen holder in that the hollow space that contains material specimens and encapsulated neutron flux monitors communicates with the exterior of the holder via at least two holes which allow reactor coolant to flow through the hollow space. One hole allows inflow of reactor coolant into the hollow space; another hole allows outflow of reactor coolant out of the hollow space. The flow is driven by the pressure differential between the inside and outside of the shroud.

DETAILED DESCRIPTION OF THE PREFERRED EMBODIMENTS

Figure 1:
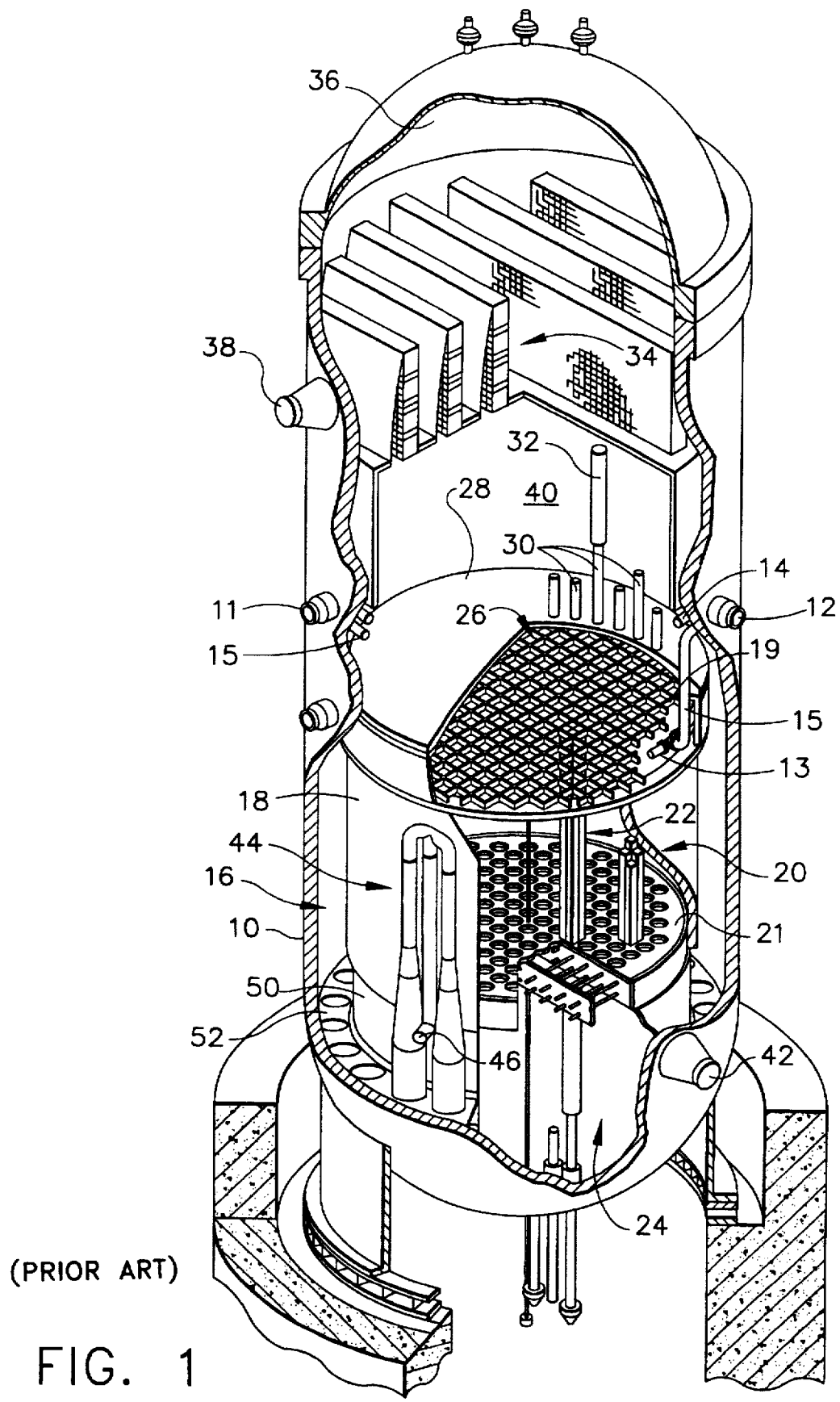
FIG. 1 is a schematic showing a partially cutaway perspective view of a conventional BWR.
Figure 2:
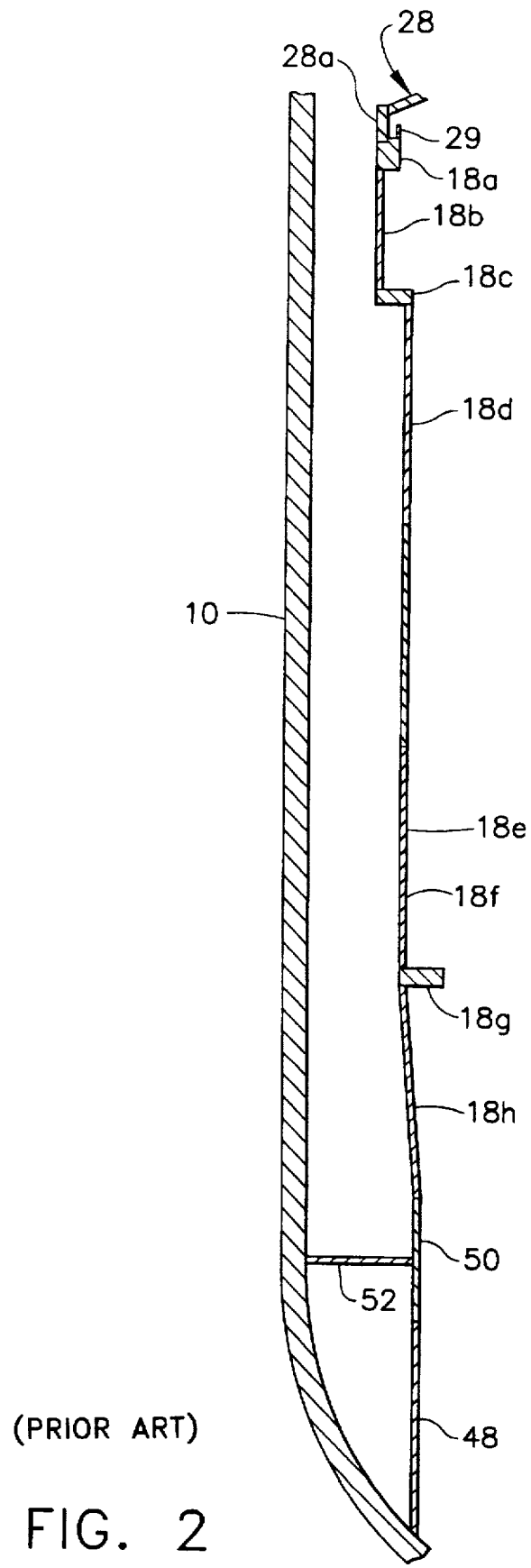
FIG. 2 is a schematic elevation view of a core shroud of one type of a BWR.
Figure 3:
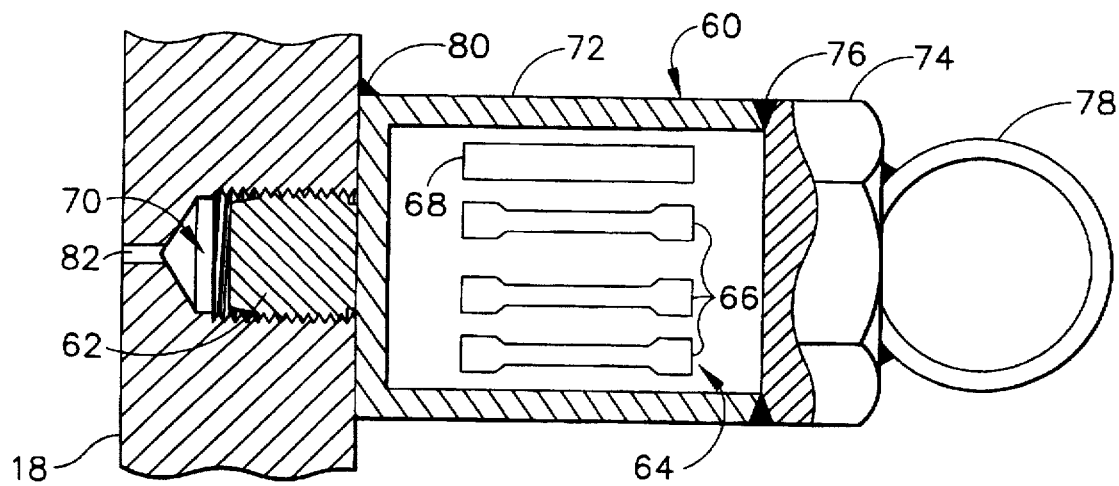
FIG. 3 is a sectional view of a leaktight shroud material specimen holder in accordance with one preferred embodiment of the invention.

Referring to FIG. 3, the preferred embodiment of the leaktight specimen holder in accordance with the present invention comprises a bolt-like device having a hollow head 60 and a threaded shaft 62. The hollow head has an interior space 64 in which material specimens 66 and encapsulated neutron flux monitors 68 are arranged. The specimen holder is attached to the shroud wall 18 by screwing the threaded shaft 62 into a threaded hole 70 formed on the inside or outside of the shroud wall. The method and apparatus for remotely tapping a threaded hole in the shroud wall are conventional and not the subject of the present invention.

In accordance with the preferred embodiment of the invention, the hollow head 60 is a welded assembly comprising a cup-shaped receptacle 72 joined at its bottom surface to the threaded shaft 62 and joined at its upper rim to a cover 74 by a peripheral weld 76. The cover 74 is a solid body having the shape of a bolt head. Preferably, cover 74 and the cup-shaped receptacle 72 have a hexagonal cross section, although polygonal shapes other than a hexagon can also be used provided that a compatible torque wrench is available.

The material specimen holder is installed remotely by an operator standing on the refueling bridge using a conventional handling pole and a suitable torquing tool. During remote manipulation of the torquing tool with a specimen holder coupled thereto, measures must be taken to ensure that the specimen holder is not accidentally dropped into the reactor. In accordance with the preferred embodiment of the specimen holder, a lifting eyelet 78 is welded to the top of cover 74. A safety hook or clasp (not shown), mounted on the end of a wire or cable suspended from the refueling bridge, can be coupled to the eyelet to secure the specimen holder in the event that the holder disengages from the torquing tool.

To attach the specimen holder to the shroud wall, first the unthreaded end of the threaded shaft 62 is guided into the threaded hole 70 and then the specimen holder is torqued until the bottom surface of the receptacle 72 bears against the shroud wall. The receptacle and shroud wall are then tack welded at sites 80 to prevent vibration-induced rotation of the specimen holder in the direction of unscrewing. Thus, the tack welds prevent the specimen holder falling out of the recess 70.

The interior space 64 of the specimen holder shown in FIG. 3 is leaktight to prevent the ingress of reactor coolant. However, a vent hole 82 is provided in the wall of shroud 18 to ensure a constant purge flow of reactor coolant through the threaded bolt hole 70 that prevents crevice corrosion. In the example where the specimen holder is mounted on an outer peripheral surface of the shroud 18, one end of vent hole 82 communicates with the threaded hole 70 and the other end communicates with the shroud interior. In this case, the reactor coolant flows from the shroud interior through vent hole 82, between the threads of shaft 62 and hole 70, into the interface between the opposing surfaces of receptacle 72 and shroud wall 18, and then into the downcoming flow in the annulus. Alternatively, if the specimen holder is mounted on an inner peripheral surface of the shroud 18, one end of vent hole 82 communicates with the threaded hole 70 and the other end communicates with the shroud exterior (i.e., the downcomer annulus). In this case, the reactor coolant flows from the shroud interior into the interface between the opposing surfaces of receptacle 72 and shroud wall 18, then between the threads of shaft 62 and hole 70, through vent hole 82, and into the shroud exterior. The purge flow in both cases is driven by the differential pressure between the inside and outside of the shroud.

Figure 4:
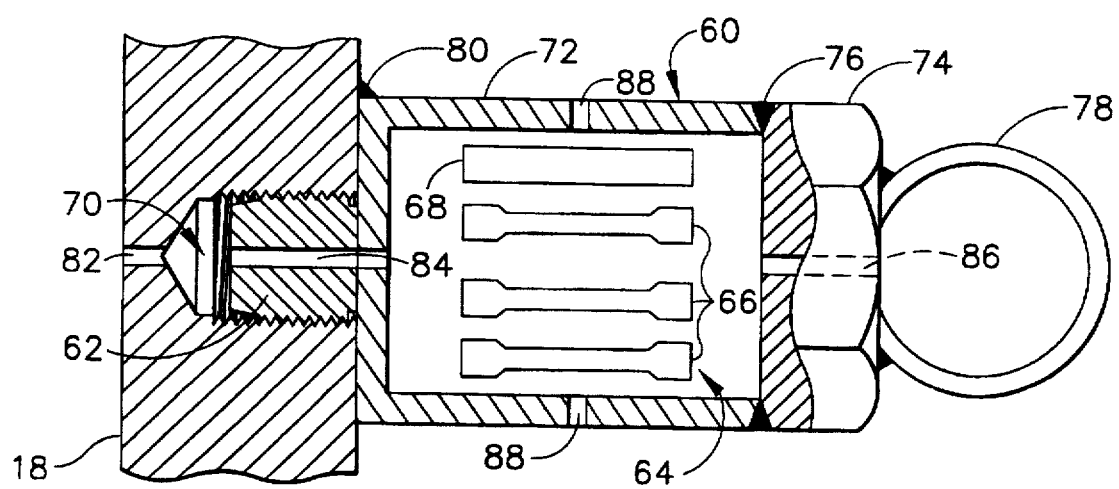
FIG. 4 is a sectional view of an open shroud material specimen holder in accordance with another preferred embodiment of the invention.

In accordance with an alternative embodiment shown in FIG. 4, the specimen holder has a container which allows the ingress of reactor coolant into the interior space 64, thereby exposing the material specimens housed therein to the oxidizing agents in the reactor coolant. This open specimen holder is similar in construction to the leaktight specimen holder shown in FIG. 3, except that the interior space 64 communicates with the space external to the hollow head 60 via vent holes. In accordance with the preferred embodiment, an axial vent hole 84 extends along a centerline of shaft 62 and through the bottom of receptacle 72. One end of vent hole 84 communicates with the interior space 64 and the other end of vent hole 84 communicates with the conical volume at the bottom of threaded hole 70. In addition, an axial vent hole 86 penetrates the cover 74 along the centerline. Lastly, two or more radial vent holes 88 penetrate the wall of the receptacle. Each of the vent holes 86 and 88 has one end which communicates with the interior space 64 and another end which communicates with either the shroud interior or the downcomer annulus, depending on whether the specimen holder is mounted on the inside or outside of the shroud. These vent holes in the specimen holder allow the reactor coolant, namely, water, to flow through the interior space 64, exposing the material specimens inside to the oxidizing agents, such as oxygen and hydrogen peroxide, dissolved in the water.

The specimen holder in accordance with the present invention provides a convenient mechanism for conducting a surveillance program to monitor IASCC in the shroud material. Material specimens made of shroud material, e.g., Type 304 stainless steel, are arranged inside the receptacle along with a neutron flux monitor. Then the cover is welded onto the receptacle to create an enclosure for the material specimens. This enclosure is attached to the inside or outside of the shroud wall at a desired elevation and kept in place for a predetermined period of reactor operation. The installation requires the steps of torquing the specimen holder into a threaded hole in the shroud wall and then tack welding the torqued holder. At the appointed time, the specimen holder is removed from the reactor by breaking the tack welds and unscrewing the specimen holder from the shroud wall. These simple operations ensure that the specimen holders can be easily retrieved from the shroud wall with a minimum of radiation exposure of plant personnel.

Once the specimen holder is out of the reactor, the hollow head is machined open and the material specimens and the neutron flux monitor are removed from the receptacle. Then the material specimens are examined in a laboratory to determine any changes in the material properties and the effect on crack growth due to exposure to the environmental conditions inside the reactor. The radiation exposure of the material specimens can be determined from the neutron flux monitor and correlated with the changes in material properties. The propagation of cracks in the material specimens can be analyzed and quantified to provide data which is useful in predicting the rate crack propagation in the core shroud.

The preferred embodiments of the shroud material specimen holders have been disclosed for the purpose of illustration. Variations and modifications of the disclosed structure which do not depart from the concept of this invention will be readily apparent to engineers skilled in the design of tooling. All such variations and modifications are intended to be encompassed by the claims set forth hereinafter.

We claim:

1. A device comprising:
   a container having at least a portion of an external surface which is in the shape of a bolt head and having an interior space;
   a threaded shaft attached to and in contact with said container; and
   a material specimen arranged inside said interior space of said container.

2. The device as defined in claim 1, wherein said material specimen is made of core shroud material.

3. The device as defined in claim 1, further comprising a neutron flux monitor arranged inside said interior space of said container.

4. The device as defined in claim 1, wherein said container has first and second vent holes arranged so that said interior space communicates with a space external to said container.

5. The device as defined in claim 1, wherein said container comprises a receptacle having an open end, a cover shaped to fit on and close said open end of said receptacle, and means for joining said cover to said receptacle, said cover having a polygonal cross section.

6. The device as defined in claim 5, wherein said joining means comprises a weld.

7. The device as defined in claim 1, further comprising an eyelet connected to said container.

8. A specimen holder comprising:
   a container having at least a portion of an external surface which is in the shape of a bolt head and having an interior space;
   a threaded shaft connected to said container;
   a material specimen arranged inside said interior space of said container; and
   a neutron flux monitor arranged inside said internal chamber of said container.

9. The specimen holder as defined in claim 8, wherein said container has first and second vent holes arranged so that said interior space communicates with a space external to said container.

10. The specimen holder as defined in claim 8, wherein said container comprises a receptacle having an open end, and a cover shaped to fit on and close said open end of said receptacle, said cover being joined to said receptacle by a weld, and said cover having a polygonal cross section.

* * * * *